United States Patent
Bittman et al.

(10) Patent No.: US 7,323,601 B2
(45) Date of Patent: Jan. 29, 2008

(54) ENANITOMERS OF UNSATURATED ALKYLLYSOPHOSPHONOCHOLINES AND USE AS ANTI-NEOPLASTICS

(75) Inventors: Robert Bittman, Roslyn Heights, NY (US); Gilbert Arthur, Winnepeg (CA); Hoe-Sup Byun, Bayside, NY (US)

(73) Assignees: Research Foundation of the City University of New York, New York, NY (US); The University of Manitoba, Winnepeg, Manitoba (CA)

( * ) Notice: Subject to any disclaimer, the term of this patent is extended or adjusted under 35 U.S.C. 154(b) by 393 days.

(21) Appl. No.: 10/468,766

(22) PCT Filed: Feb. 21, 2002

(86) PCT No.: PCT/US02/04972

§ 371 (c)(1),
(2), (4) Date: Jul. 7, 2004

(87) PCT Pub. No.: WO02/067855

PCT Pub. Date: Sep. 6, 2002

(65) Prior Publication Data

US 2005/0014971 A1 Jan. 20, 2005

Related U.S. Application Data

(60) Provisional application No. 60/270,308, filed on Feb. 21, 2001.

(51) Int. Cl.
*C07F 9/22* (2006.01)
*C07F 9/28* (2006.01)

(52) U.S. Cl. .............................. 568/8; 568/13; 568/14

(58) Field of Classification Search .................... None
See application file for complete search history.

(56) References Cited

U.S. PATENT DOCUMENTS 2,605,280 A  7/1952  Klotz et al.

*Primary Examiner*—Yvonne Eyler
*Assistant Examiner*—Yevgeny Valenrod
(74) *Attorney, Agent, or Firm*—Nixon & Vanderhye P.C.

(57) ABSTRACT

Unsaturated alkyllysophosphonocholines compounds of formula (I) or (II):

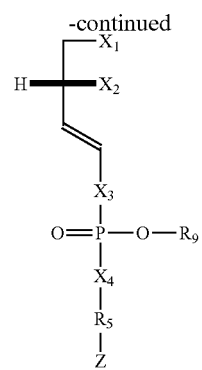

or pharmaceutically-acceptable salts, prodrugs or isomers thereof. The compounds of the invention have anti-neoplastic activity, and accordingly have utility in treating cancer and related diseases. The invention also provides enantiomers of these compounds, as well as synthetic methods for producing an enantiomer, substantially free of the other enantiomer. Also disclosed are pharmaceutical compositions, as well methods for treating cancer with the pharmaceutical compositions.

44 Claims, 7 Drawing Sheets

ENANTIOMERS OF UNSATURATED ALKYLLYSOPHOSPHONOCHOLINES AND USE AS ANTI-NEOPLASTICS

INCORPORATION BY REFERENCE

This application claims priority of U.S. provisional application Ser. No. 60/270,308, filed on Feb. 21, 2001, the entire contents of which are incorporated herein by reference.

BACKGROUND OF THE INVENTION

1. Field of the Invention

The present invention provides novel unsaturated alkyllysophosphonocholines compounds and enantiomers thereof, as well as pharmaceutical compositions thereof, and methods for treating cancer. Synthetic methods for synthesizing enantiomers of the compounds is also provided.

2. State of the Art

Alkyllysophospholipids (ALPs) and alkylphosphocholines (APCs) represent subclasses of potential antitumor agents collectively known as antitumor ether lipids (AELs). They do not interact with cellular DNA and are therefore not mutagenic (Berdel, W. E. (1991) *Br. J Cancer*, 64, 208-211; Lohmeyer, M., and Bittman, R. (1994) *Drugs of the Future* 19, 1021-1037). The antitumor activities of these compounds, which are based on lysophosphatidylcholine, are now well established; the prototype of the alkyllysophospholipids (ALPs), 1-O-octadecyl-2-O-methyl-glycerophosphocholine (ET-18-OCH$_3$), and other ether-linked phosphocholine analogues are in clinical trials (Lohmeyer, M., and Bittman, R. (1994) *Drugs of the Future* 19, 1021-1037, Houlihan, W. J., Lohmeyer, M., Workman, P., and Cheon, S. H. (1995) *Med Res. Rev.* 15, 157-223; Principe, P., and Braquet, P. (1995) *Rev. Oncol. Hematol.* 18, 155-178).

ALPs also appear to inhibit the proliferation of tumor cells without affecting the growth of normal cells (Berdel, W. E., Andreesen, R., and Munder, P. G. (1985) in *Phospholipids and Cellular Regulation, Vol 2*. Kuo, J (ed). CRC Press: Boca Raton, pp. 41-73). While the mechanism of inhibition of cell proliferation has yet to be resolved, various hypotheses have been proposed. In some cells, ALPs and APCs appear to induce apoptosis as a consequence of inhibition of phosphatidylcholine synthesis (Boggs, K. P., Rock, C. O., and Jackowski, S. (1995) *J Biol. Chem.* 270, 11612-11618; Boggs, K. P., Rock, C. O., and Jackowski, S. (1998) *Biochim. Biophys. Acta* 1389, 1-12); activation of the stress activated protein kinase pathways (Gajate, C., Santos-Beneit, A., Modolell, M., and Mollinedo, F. (1998) *Mol. Pharmacol.* 53, 602-612; Ruiter, G. A., Zerp, S. F., Bartelink, H., Van Blitterswijk, W. J., and Verheij, M. (1999) *Cancer Res.* 59, 2457-2463), drug-induced increase in cellular ceramide levels (Wieder, T., Orfanos, C. E., and Geilen, C. G. (1998) *J. Biol. Chem.* 273, 11025-11031); nutrient starvation, inhibition of transacylase activity, enhanced lipid peroxidation and inhibition of cellular signaling pathways (reviewed in Bittman, R., and Arthur, G. (1998) in A. S. Janoff (ed.), *Liposomes: Rational Design*, pp 125-144, New York: Marcel Dekker; Arthur; G., and Bittman, R. (1998) *Biochim. Biophys. Acta* 1390, 85-102).

Other studies have revealed that ALPs affect the activity of a large number of signaling molecules including protein kinase C (PKC), phosphatidylinositol 3-kinase, phosphatidylinositol-specific phospholipase C, and diacylglycerol kinase (reviewed in Arthur, G., and Bittman, R. (1998) *Biochim. Biophys. Acta* 1390, 85-102). Recently another signaling molecule, Raf-1, was added to the list with the demonstration that ET-18-OCH$_3$ decreased the levels of Raf-1 associating with the cell membrane in growth-factor stimulated MCF-7 cells which consequently led to decreased activation of MAP kinase (Zhou, X., Lu, X., Richard, C., Xiong, W., Litchfield, D. W., Bittman, R., and Arthur, G. (1996) *J Clin. Invest.* 98, 937-944), a crucial enzyme required in initiating cell proliferation (Marshall, C. J. (1995) *Cell* 80, 179-185). It was suggested that Raf-1 is a primary target of ALPs in cells. The large number of molecules affected by ALPs has complicated the task of separating their primary site(s) of action from secondary events. In order to advance the present understanding of the mechanism(s) of action of these compounds, one has to distinguish target molecules and events that are relevant to growth inhibition from those that are irrelevant.

Despite the progress that has been made in understanding the underlying mechanisms of antitumor ether lipids, there remains a need to develop novel compounds and compositions for treatment of disease. Ideally, the treatment methods would advantageously be based on anti-tumor ether lipids that are capable of acting as anti-neoplastic agents.

SUMMARY OF THE INVENTION

The invention is directed to the discovery of a class of anti-tumor ether lipid compounds having anti-neoplastic activity. Preferably, the invention provides bioactive unsaturated alkyllysophosphonocholines or pharmaceutically-acceptable salts, prodrugs or isomers thereof having the R or S configuration at the C-2 position of the glycerol backbone. The invention also relates to pharmaceutical compositions comprising these compounds, and methods for treating cancer.

Neither the R enantiomer nor S enantiomer of a trans double bond (TBD) phosphonocholine etherlipid, an analogue of ET-16-OCH$_3$, 2'-(trimethylammonio)ethyl 4-(hexadecyloxy)-3-methoxy-1-butenephosphonate [ET-16-phosphono-TDB], has previously been synthesized. In order to differentiate the activities of each of these enantiomers, single enantiomers must be available in sufficient chiral purity to enable a comparison of the chemical, biological and biochemical effects of the single enantiomers. Thus, until the present invention nothing was known about the antineoplastic effects of the single R and S enantiomers of phosphono etherlipids, in general, and ET-16-phosphono-TDB specifically.

In one embodiment, the invention relates to compounds, or a pharmaceutically acceptable salt, prodrug or isomer thereof, having formula I below:

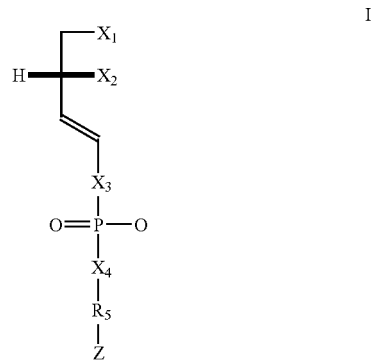

wherein $X_1$ is H, $R_1$, $R_2$, $OR_2$, $NR_1R_2$, or $S(O)_aR_2$, where a is an integer selected from 0, 1, 2, or 3;

$X_2$ is H, $R_3$, $R_4$, $OR_4$, $NR_3R_4$, or $S(O)_aR_4$, where a is an integer selected from 0, 1, 2, or 3;

$X_3$ is $(CH_2)_b$, where b is an integer selected from 0, 1, 2, 3, or 4;

$X_4$ is $(CH_2)_c$, where c is an integer selected from 0, 1, 2, 3, or 4;

$R_1$ is a straight-chain or branched alkyl having 12 to 20 carbon atoms or a straight-chain or branched alkenyl group having 12 to 20 carbon atoms;

$R_2$ is H, a straight-chain or branched alkyl having 12 to 20 carbon atoms or a straight-chain or branched alkenyl group having 12 to 20 carbon atoms;

$R_3$ is a straight-chain alkyl group having 1 to 3 carbon atoms, or a branched or cyclic alkyl group having 3 carbon atoms;

$R_4$ is H, a straight-chain alkyl group having 1 to 3 carbon atoms, or a branched or cyclic alkyl group having 3 carbon atoms;

$R_5$ is $(CH_2)_m$ where m is an integer selected from 0, 1, 2, 3, or 4;

Z is H,

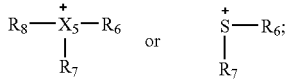

$X_5$ is N or As;

$R_6$ and $R_7$ are each independently hydrogen, a straight-chain alkyl group having 1 to 3 carbon atoms, or a branched or cyclic alkyl group having 3 carbon atoms; and $R_8$ is hydrogen, a straight-chain alkyl-group having 1 to 3 carbon atoms or a branched or cyclic alkyl group having 3 carbon atoms.

In another embodiment, the invention relates to compounds of formula II, or a pharmaceutically acceptable salt, prodrug or isomer thereof:

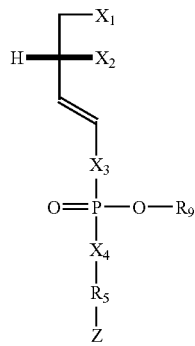

wherein $X_1$ is H, $R_1$, $R_2$, $OR_2$, $NR_1R_2$, or $S(O)_aR_2$, where a is an integer selected from 0, 1, 2, or 3;

$X_2$ is H, $R_3$, $R_4$, $OR_4$, $NR_3R_4$, or $S(O)_aR_4$, where a is an integer selected from 0, 1, 2, or 3;

$X_3$ is $(CH_2)_b$, where b is an integer selected from 0, 1, 2, 3, or 4;

$X_4$ is $(CH_2)_c$, where c is an integer selected from 0, 1, 2, 3, or 4;

$R_1$ is a straight-chain or branched alkyl having 12 to 20 carbon atoms or a straight-chain or branched alkenyl group having 12 to 20 carbon atoms;

$R_2$ is H, a straight-chain or branched alkyl having 12 to 20 carbon atoms or a straight-chain or branched alkenyl group having 12 to 20 carbon atoms;

$R_3$ is a straight-chain alkyl group having 1 to 3 carbon atoms, or a branched or cyclic alkyl group having 3 carbon atoms;

$R_4$ is H, a straight-chain alkyl group having 1 to 3 carbon atoms, or a branched or cyclic alkyl group having 3 carbon atoms;

$R_5$ is $(CH_2)_m$ where m is an integer selected from 0, 1, 2, 3, or 4;

Z is H,

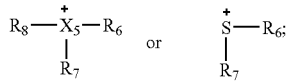

$X_5$ is N or As;

$R_6$ and $R_7$ are each independently hydrogen, a straight-chain alkyl group having 1 to 3 carbon atoms, or a branched or cyclic alkyl group having 3 carbon atoms;

$R_8$ is hydrogen, a straight-chain alkyl group having 1 to 3 carbon atoms or a branched or cyclic alkyl group having 3 carbon atoms; and $R_9$ is a straight-chain alkyl group having 1 to 3 carbon atoms or a branched or cyclic alkyl group having 3 carbon atoms.

The compounds of formula (I) or (II) above may further comprise a pharmaceutically acceptable anion. Preferably, $R_1$ and $R_2$ are independently a straight-chain or branched alkyl having 16 to 20 carbon atoms, or a straight-chain or a branched alkenyl group having 16 to 20 carbon atoms. In another preferred embodiment, $R_1$ and $R_2$ are independently a straight-chain or branched alkyl having 18 carbon atoms, or a straight-chain or a branched alkenyl group having 18 carbon atoms.

In an embodiment of the invention, $X_1$ is $OR_2$ or $NHR_2$, where $R_2$ is a straight-chain or branched alkyl having 16 to 20 carbon atoms, or a straight-chain or a branched alkenyl group having 16 to 20 carbon atoms. In a preferred embodiment, $R_2$ is a straight-chain or branched alkyl having 18 carbon atoms, or a straight-chain or a branched alkenyl group having 18 carbon atoms.

In an embodiment of the invention, $X_1$ or $X_2$ is independently selected from —$SR_2$, —$S(=O)R_2$, —$S(=O)_2R_2$, —$S(=O)_2OR_2$, or —$OS(=O)_2R_2$.

In an embodiment of the invention, $X_1$ or $X_2$ is —$OCH_3$.

Typical values for $X_3$, $X_4$, and $R_5$ include a direct link, a —$CH_2$— group, or a —$CH_2CH_2$— group.

Preferred values for Z include

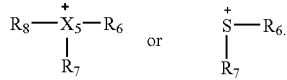

Yet another embodiment of the invention relates to compounds where $X_1$ is O, $X_2$ is O, $X_4$ is O and b is 0. The invention also relates to optically active compounds of formula (I) or (II), which are substantially free of the R enantiomer. In addition, the invention also relates to optically active compounds of formula (I) or (II), which are substantially free of the S enantiomer. For example, the invention relates to 2'-(trimethylammonio)ethyl 4-(hexadecyloxy)-3-(S)-methoxy-1-butenephosphonate substantially free of the R enantiomer, as well as 2'-(trimethylammonio)ethyl 4-(hexadecyloxy)-3-(S)-methoxy-1-butenephosphonate substantially free of the S enantiomer.

Additionally, the invention relates to pharmaceutical compositions comprising a pharmaceutically acceptable carrier and a pharmaceutically effective amount of a compound of formula (I) or (II). These pharmaceutical compositions can be used in methods for treating a mammal afflicted with a cancer, comprising administering to the mammal a therapeutically effective amount of the pharmaceutical composition. Typical dosages range from about 0.1 to about 1000 mg of the compound of formula (I) or (II) per kg of the body weight of the mammal per day.

The type of cancer to be treated may be selected from the group consisting of, but not limited to: lung cancers, brain cancers, colon cancers, ovarian cancers, breast cancers, leukemias, lymphomas, sarcomas, and carcinomas. These treatment methods may also include administering to the mammal an additional biologically active agent. The additional biologically active agent may be selected from the group consisting of antineoplastic agents, antimicrobial agents, and hematopoietic cell growth stimulating agents, for example.

In addition, the invention relates to a method for making 2'-(trimethylammonio)ethyl 4-(hexadecyloxy)-3-(S)-methoxy-1-butenephosphonate substantially free of the (R) enantiomer, comprising:
(i) oxidizing 1-O-hexadecyl-2-O-methyl-sn-glycerol under Swern oxidation conditions sufficient to produce (S)-1-O-hexadecyl-2-O-methoxyglyceraldehyde;
(ii) reacting the (S)-1-O-hexadecyl-2-O-methoxyglyceraldehyde with tetraisopropyl methylenediphosphonate under conditions sufficient to produce diisopropyl 4-(hexadecyloxy)-3-(S)-methoxy-1-butenephosphonate;
(iii) hydrolyzing the diisopropyl 4-(hexadecyloxy)-3-(S)-methoxy-1-butenephosphonate under conditions sufficient to produce the 4-(hexadecyloxy)-3-(S)-methoxy-1-butenephosphonic acid; and
(iv) reacting the diisopropyl 4-(hexadecyloxy)-3-(S)-methoxy-1-butenephosphonate with choline tosylate under conditions sufficient to produce 2'-(trimethylammonio)ethyl 4-(hexadecyloxy)-3-(S)-methoxy-1-butenephosphonate.

The invention also relates to a method for making 2'-(trimethylammonio)ethyl 4-(hexadecyloxy)-3-(S)-methoxy-1-butenephosphonate substantially free of the (S) enantiomer, comprising:
(i) oxidizing 3-O-hexadecyl-2-O-methyl-sn-glycerol under Swern oxidation conditions sufficient to produce (S)-1-O-hexadecyl-2-O-methoxyglyceraldehyde;
(ii) reacting the (S)-1-O-hexadecyl-2-O-methoxyglyceraldehyde with tetraisopropyl methylenediphosphonate under conditions sufficient to produce diisopropyl 4-(hexadecyloxy)-3-(S)-methoxy-1-butenephosphonate;
(iii) hydrolyzing the diisopropyl 4-(hexadecyloxy)-3-(S)-methoxy-1-butenephosphonate under conditions sufficient to produce the 4-(hexadecyloxy)-3-(S)-methoxy-1-butenephosphonic acid; and
(iv) reacting the diisopropyl 4-(hexadecyloxy)-3-(S)-methoxy-1-butenephosphonate with choline tosylate under conditions sufficient to produce 2'-(trimethylammonio)ethyl 4-(hexadecyloxy)-3-(S)-methoxy-1-butenephosphonate.

DETAILED DESCRIPTION OF THE INVENTION

Figure 1:
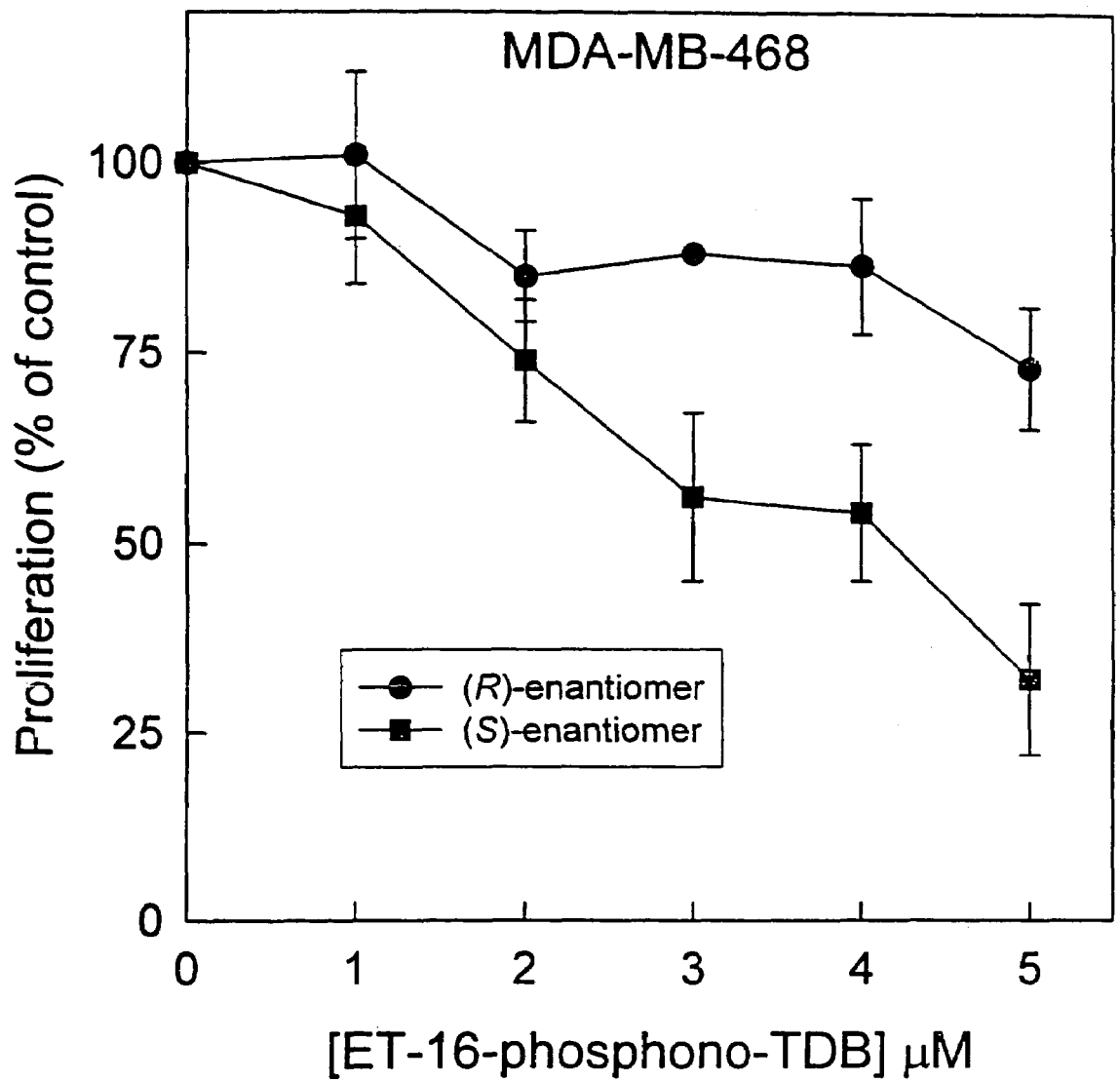
FIG. 1. Graphical depiction of the effects of (R) and (S) ET-16-phosphono-TDB on the proliferation of breast epithelial cancer cell line MDA-MB-468.

As above, this invention relates to unsaturated alkyllysophosphonocholines or pharmaceutically-acceptable salts, prodrugs, or isomers thereof, which have utility as antineoplastic agents. In particular, the invention relates to compounds of formula (I) and (II), having the R or S configuration at the C-2 position of the glycerol backbone, substantially free of the other enantiomer. However, prior to describing this invention in further detail, the following terms will first be defined.

DEFINITIONS

The term "alkyl" refers to saturated aliphatic groups including straight-chain, branched-chain, cyclic groups, and combinations thereof. The alkyl groups preferably have between 1 to 20 carbon atoms.

The term "alkenyl" refers to unsaturated aliphatic groups including straight-chain, branched-chain, cyclic groups, and combinations thereof, having at least one double bond and having the number of carbon atoms specified. The alkenyl groups preferably have between 1 to 20 carbon atoms.

The term "cyclic alkyl" or "cycloalkyl" refers to alkyl group forming an aliphatic ring. Preferred cyclic alkyl groups have about 3 carbon atoms.

The term "direct link" as used herein refers to a bond directly linking the substituents on each side of the direct link.

"Pharmaceutically acceptable salt" refers to pharmaceutically acceptable salts that are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. Examples of pharmaceutically acceptable acid addition salts includes salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Examples of pharmaceutically acceptable base addition salts include those salts derived from inorganic bases such as sodium, potassium, lithium, ammonium, calcium, magnesium, iron, zinc, copper, manganese, and aluminum bases, and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Prodrug" means any compound which releases an active parent drug according to formulas (I) or (II) in vivo when such prodrug is administered to a mammalian subject. Prodrugs of a compound may be prepared by modifying functional groups present in the compound in such a way that the modifications may be cleaved in vivo to release the parent compound. Prodrugs include compounds of formula (I) or (II) wherein a hydroxy, amino, or sulfhydryl group is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylamino-carbonyl), and the like.

"Isomers" are compounds that have the same molecular formula but differ in the nature or sequence of bonding of their atoms or the arrangement of their atoms in space. Isomers that differ in the arrangement of their atoms in space are termed "stereoisomers." Stereoisomers that are not mirror images of one another are termed "diastereomers" and those that are non-superimposable mirror images of each other are termed "enantiomers." An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A "pharmaceutically acceptable carrier" means an carrier that is useful in preparing a pharmaceutical composition that is generally safe, non-toxic and neither biologically nor otherwise undesirable, and includes a pharmaceutically acceptable excipient that is acceptable for veterinary use or human pharmaceutical use. A "pharmaceutically acceptable excipient" as used in the specification and claims includes both one and more than one such excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

"Cancer" refers to a group of diseases characterized by uncontrolled growth and spread of abnormal cells, often resulting in the formation of a non-structured mass or tumor. Illustrative tumors include carcinomas, sarcomas and melanomas, such as basal cell carcinoma, squamous cell carcinoma, melanoma, soft tissue sarcoma, solar keratoses, Kaposi's sarcoma, cutaneous malignant lymphoma, Bowen's disease, Wilm's tumor, hepatomas, colorectals cancer, brain tumors, mycosis fungoides, Hodgkin's lymphoma, polycythemia Vera, chronic granulocytic leukemia, lymphomas, oat cell sarcoma, and the like. Tumors may also include benign growths such as condylomata acuminata (genital warts) and moles and common warts.

An "anti-neoplastic agent" is a pharmaceutical which inhibits or causes the death of cancer or tumor cells.

An "antimicrobial agent" is a substance that either destroys or inhibits the growth of a microorganism at concentrations tolerated by the infected host.

A "hematopoietic cell growth stimulating agent" is one that stimulates blood cell growth and development, i.e. of red blood cells, leukocytes, and , platelets. Such agents are well known in the art. For example, in order to increase infection-fighting white blood cell production, recombinant granulocyte-colony stimulating factor may be used to stimulate the growth of neutrophils. Another example of a hematopoietic cell growth stimulating agent is recombinant granulocyte macrophage-colony stimulating factor, which increases production of neutrophils, as well as other infection-fighting white blood cells, granulocytes and monocytes, and macrophages. Another hematopoietic agent is recombinant stem cell factor, which regulates and stimulates the bone marrow, specifically to produce stem cells.

Pharmaceutical Formulations

When employed as pharmaceuticals, the compounds of formulas (I) and (II) are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula (I) or (II) above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula (I) or (II) above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner. The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard-gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
|---|---|
| Active Ingredient | 5.0 mg |
| Corn Oil | 1.0 mL |

FORMULATION EXAMPLE 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference in its entirety.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17th ed. (1985).

Utility

The compounds and pharmaceutical compositions of the invention are useful as anti-neoplastic agents, and accordingly, have utility in treating cancer in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from cancer in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of cancer in the patient, the age, weight and general condition of the patient, and the like. Preferably, for use as therapeutics, the compounds described herein are administered at dosages ranging from about 0.1 to about 500 mg/kg/day.

In prophylactic applications, compositions are administered to a patient at risk of developing cancer (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 0.1 to about 500 mg/kg/day.

As noted above, the compounds administered to a patient are in the form of pharmaceutical compositions described above. These compositions may be sterilized by conventional sterilization techniques, or may be sterile filtered. When aqueous solutions are employed, these may be packaged for use as is, or lyophilized, the lyophilized preparation being combined with a sterile aqueous carrier prior to administration. The pH of the compound preparations typically will be between 3 and 11, more preferably from 5-9 and most preferably from 7 and 8. It will be understood that use of certain of the foregoing excipients, carriers, or stabilizers will result in the formation of pharmaceutical salts.

Specific embodiments of the invention will now be described through examples. The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

bd=broad doublet
bs=broad singlet
c=concentration
d=doublet
dd=doublet of doublets
ddd=doublet of doublets of doublets
DMF=dimethylformamide
DMSO=dimethyl sulfoxide
g=grams
hept.=heptuplet
J=coupling constant
m=multiplet
M=molar
max=maximum
mg=milligram
min.=minutes
mL=milliliter
mM=millimolar
mmol=millimole
N=normal
ng=nanogram
nm=nanometers
OD=optical density
q=quartet
s=singlet
sept=septuplet
t=triplet
THF=tetrahydrofuran
tlc=thin layer chromatography
μL=microliter The antibodies were obtained from the following vendors: Transduction Laboratories, Lexington, Ky. (Raf-1, PKB/AKT); New England Biolabs Inc, Beverly, Mass. (phospho-MAP kinase and phospho-PKB/AKT); Santa Cruz Inc, Santa Cruz, Calif. (ERK-1, ERK-2); fetal bovine serum (FBS) from Hyaclone (Logan, Utah).

Additionally, the term "Aldrich" indicates that the compound or reagent used in the following procedures is commercially available from Aldrich Chemical Company, Inc., .1001 West Saint Paul Avenue, Milwaukee, Wis. 53233 USA; the term "Fluka" indicates the compound or reagent is commercially available from Fluka Chemical Corp., 980 South 2nd Street, Ronkonkoma, N.Y. 11779 USA; the term "Lancaster" indicates the compound or reagent is commercially available from Lancaster Synthesis, Inc., P.O. Box 100, Windham, N.H. 03087 USA; and the term "Sigma" indicates the compound or reagent is commercially available from Sigma, P.O. Box 14508, St. Louis, Mo. 63178 USA.

Unless otherwise stated, all temperatures are in degrees Celsius.

NMR spectra were recorded on an IBM-Bruker 200-MHz or a Bruker 400-MHz Spectrometer with Me$_4$Si as internal standard. Infrared spectra were recorded on a Perkin-Elmer 1600 FT spectrophotometer. Optical rotations were measured on a JASCO Model DIP-140 digital polarimeter-using a 1-dm cell. Methylene chloride and pyridine were distilled from calcium hydride and barium oxide, respectively. Chloroform was distilled from P$_2$O$_5$. All other synthetic reagents were used as received unless otherwise stated.

In these synthetic methods, the starting materials can contain a chiral center and, when a racemic starting material is employed, the resulting product is a mixture of R,S enantiomers. Alternatively, a chiral isomer of the starting material can be employed and, if the reaction protocol employed does not racemize this starting material, a chiral product is obtained. Such reaction protocols can involve inversion of the chiral center during synthesis. Alternatively, chiral products can be obtained via purification techniques which separates enantiomers from a R,S mixture to provide for one or the other stereoisomer. Such techniques are well known in the art.

The compounds of formula (I) or (II) may be synthesized using the methods ememplified in the examples. Such method may be adapted to produce analogs, derivatives and variants within the scope of formula (I) or (II). The compounds of formula (I) or (II) can also be prepared via several divergent synthetic routes with the particular route selected relative to the ease of compound preparation, the commercial availability of starting materials, and the like.

Example 1

Preparation of the S and R ET-16-phosphono-TDB stereoisomers

2'-(Trimethylammonio)ethyl 4-(hexadecyloxy)-3-(S)-methoxy-1-butenephosphonate [(S)-ET-16-phosphono-TDB] was synthesized in 91% enantiomeric excess from 1-O-hexadecyl-2-O-methyl-sn-glycerol (Byun, H-S., Kumar, E. R., and Bittman, R. (1994) *J Org. Chem.* 59, 2630-2633). Swern oxidation of the latter compound was carried out as follows: Dimethyl sulfoxide (1.85 mL, 21.4 mmol) was added to a solution of oxalyl chloride (1.0 mL, 11.5 mmol) in 150 mL of methylene chloride at −78° C. After 10 min, 1-O-hexadecyl-2-O-methyl-sn-glycerol (3.31 g, 10.0 mmol) in 20 mL of methylene chloride was added, and the reaction mixture was stirred for 1 h at −78° C., followed by the addition of triethylamine (7.0 mL, 50 mmol). After 1 h at −78° C., the mixture was warmed to room temperature, diluted with diethyl ether, and washed with water, 10% aqueous sodium bisulfate solution, and brine solution. The organic phase was dried over sodium sulfate and concentrated to give crude (S)-1-O-hexadecyl-2-O-methoxyglyceraldehyde. Tetraisopropyl methylenediphosphonate (3.44 g, 10 mmol) was added to a suspension of sodium hydride (0.3 g, 10 mmol, 85% in white oil, washed with dry hexane twice) in 50 mL of dry THF at 0° C. After cessation of H$_2$ evolution, a solution of the crude aldehyde in 10 mL of THF was added and the mixture was stirred overnight at 0° C. The mixture was concentrated under reduced pressure and the residue was dissolved in diethyl ether and washed with water and brine. The organic phase was dried over sodium sulfate and concentrated. The residue was purified by column chromatography on silica gel (elution with chlorofonn-methanol 50:1) to give 4.31 g of pure diisopropyl 4-(hexadecyloxy)-3-(S)-methoxy-1-butenephosphonate (88%) as a pale yellow oil; $[\alpha]^{25}_D$ −3.14° (c 50.8, CHCl$_3$); IR (film) 2356, 1361, 1115, 1061, 1020 cm$^{-1}$; $^1$H NMR (CDCl$_3$) δ 6.65 (dt, 1H, J=5.1, 17.2 Hz), 5.98 (dd, 1H, J=17.2,20.1 Hz), 4.59-4.73 (m, 1H), 3.38-3.96 (m, 6H), 3.47 (s, 3H), 1.32-1.35 (m, 2H), 1.32 (s, 12H), 1.26 (s, 26H), 0.88 (t, 3H, J=5.6 Hz); $^{13}$C NMR (CDCl$_3$) δ 153.21, 152.95; Anal. Calcd for C$_{27}$H$_{55}$O$_5$P: C, 66.09; H, 11.30; P, 6.31. Found: C, 66.21; H, 11.22; P, 6.26.

The butenephosphonate (246 mg, 0.50 mmol) was dissolved in 10 mL of methylene chloride followed by the addition of bromotrimethylsilane (1.3 mL, 2.7 mmol) and stirring for 2 h at room temperature. Volatile materials were removed in vacuo, the residue was dissolved in THF-water (10 mL, 9:1 by volume), and the mixture was allowed to stand for 2 h at room temperature to complete the hydrolysis of the isopropyl ester groups. The solvents were removed under vacuum, and the residue was dried with the aid of dry 2-propanol followed by lyophilization from benzene to give the corresponding phosphonic acid.

A solution of the phosphonic acid, choline tosylate (0.30 g, 0.90 mmol), and trichloroacetonitrile (0.30 mL, 3.0 mmol) in 20 mL of pyridine was heated for 48 h at 50° C. After most of pyridine was removed under reduced pressure, a dark brown semi-solid residue was obtained. It was dissolved in THF-water (9:1 by volume) and passed through a column of Amberlite MB-3 ion exchange resin, which was previously equilibrated with THF-water (9:1). Pure phosphonocholine was obtained after chromatography on silica gel column two times, eluting with chloroform-methanol-water (65:35:4); 150 mg (61% yield, after filtration of a solution of the product in chloroform through Cameo filters to remove suspended silica gel); $[α]^{25}_D$ −2.32° (c 9.1, CHCl$_3$—CH$_3$OH, 1:1); IR (film) 3355, 1361, 1100 cm$^{-1}$; $^1$H NMR (400 MHz, CHCl$_3$—CD$_3$OD) δ 6.35 (ddd, 1H, J=5.80, 17.32, 20.17 Hz), 5.98 (dd, 1H, J=17.32,17.56 Hz), 4.05 (s, 3H), 3.90-3.93 (m, 1H), 3.65-3.68 (m, 2H), 3.42-3.48 (m, 4H), 3.41 (s, 2H), 3.26 (s, 9H), 1.54-1.58 (m, 2H), 1.26 (s, 26H), 0.88 (t, 3H, J=6.64 Hz); $^{13}$C NMR (100 MHz, CHCl$_3$—CD$_3$OD) δ 142.82, 125.43 (d, $J^1_{H^{-31}P}$=186.6 Hz), 81.12 (d, $J^1_{H^{-31}P}$=20.1 Hz), 73.00, 71.71 66.63, 57.69, 57.21, 54.35, 31.81, 29.58, 29.54, 29.46, 29.41, 25.92, 22.57, 13.98. Anal. Calcd for C$_{26}$H$_{54}$O$_5$P.2H$_2$O: C, 59.18; H, 11.08; N, 2.65; P, 5.87. Found: C, 59.20; H, 11.11; N, 2.44; P, 5.66.

2'-(Trimethylammonio)ethyl 4-(hexadecyloxy)-3-(R)-methoxy-1-butenephosphonate [(R)-ET-16-phosphono-TDB] was synthesized from 3-O-hexadecyl-2-O-methyl-sn-glycerol in 59% yield by analogous procedures to those described above; $[α]^{25}_D$+2.67° (c 23.1, CHCl$_3$—CH$_3$OH, 1:1). The $^1$H and $^{13}$C NMR spectra were identical to those of the S enantiomer.

Stock solutions (30 mM) of (R)-ET-16-phosphono-TDB and (S)-ET-16-phosphono-TDB in absolute ethanol were kept at −20° C. The structures of (R) and (S)-ET-16-phosphono-TDB are as follows:

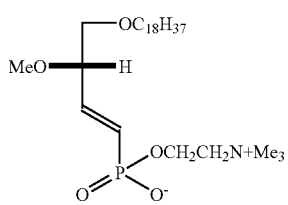

(R)-ET-16-phosphono-TDB

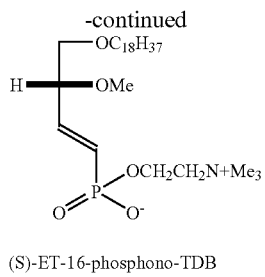

(S)-ET-16-phosphono-TDB

Example 2

Cell Culture

All the cell lines were grown from frozen stocks originally obtained from ATCC. T47D, MDA-MB-468 and MCF-7 (breast cancer cell lines) were grown in DMEM. SK-N-MC and SK-N-SH (neuroblastoma) were grown in minimum essential medium with non-essential amino acids and Earle's balanced salt solution. All media were supplemented with 10% FBS and antibiotics (Ashagbley, A., Samadder, P., Bittman, R., Erukulla, R. K., Byun, H-S., Arthur, G. (1 996) *Anticancer Res.* 16, 1813-1818).

Example 3

Effect of Ether Lipids on the Proliferation of Log-phase Epithelial Cells

The effect of the ET-16-phosphono-TDBs on cell proliferation was conducted as previously described (Ashagbley, A., Samadder, P., Bittman, R., Erukulla, R. K., Byun, H-S., Arthur, G. (1996) *Anticancer Res.* 16, 1813-1818; and Lu, X., and Arthur, G. (1992) *Cancer Res.* 52, 2806-2812). The cells were seeded in 24-well dishes at a density of 20,000 cells/well with 10% FBS-supplemented medium. The cell numbers were monitored daily. When growth was exponential, the medium was removed and replaced with 10% FBS-supplemented medium containing different concentrations (0-5 μM) of (R) or (S)-ET-16-phosphono-TDB. The cell numbers at the time of addition of the drugs were determined with a Coulter ZM counter. After 48 h incubation, the cell numbers were determined and the increase in cell number over the numbers at the time of the addition of the drugs was determined and expressed as a function of the control cells which received no drug. The viability of the cells was assessed by the ability to exclude trypan blue dye.

Figure 2:
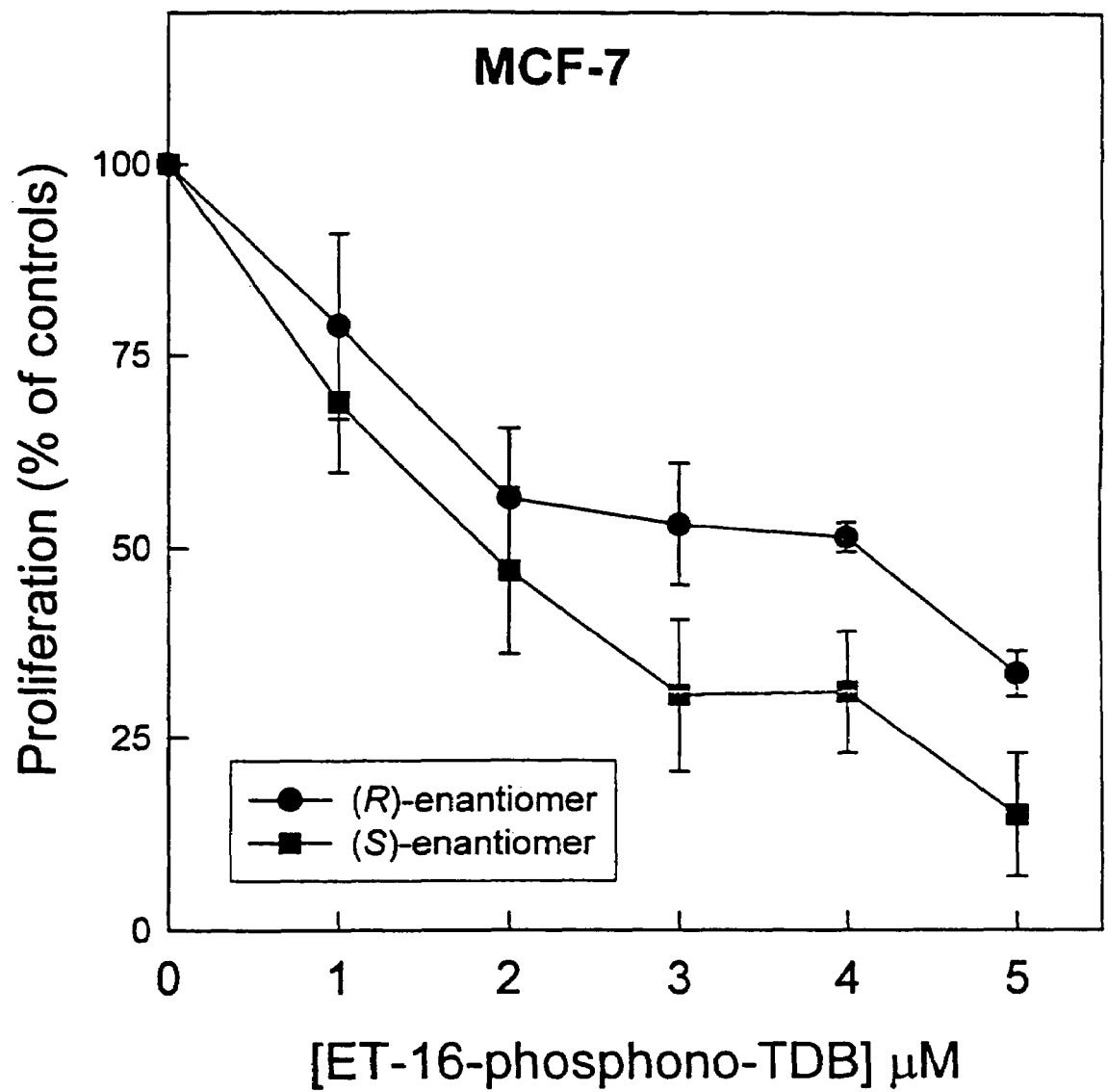
FIG. 2. Graphical depiction of the effects of (R) and (S) ET-16-phosphono-TDB on the proliferation of breast epithelial cancer cell line MCF-7.
Figure 3:
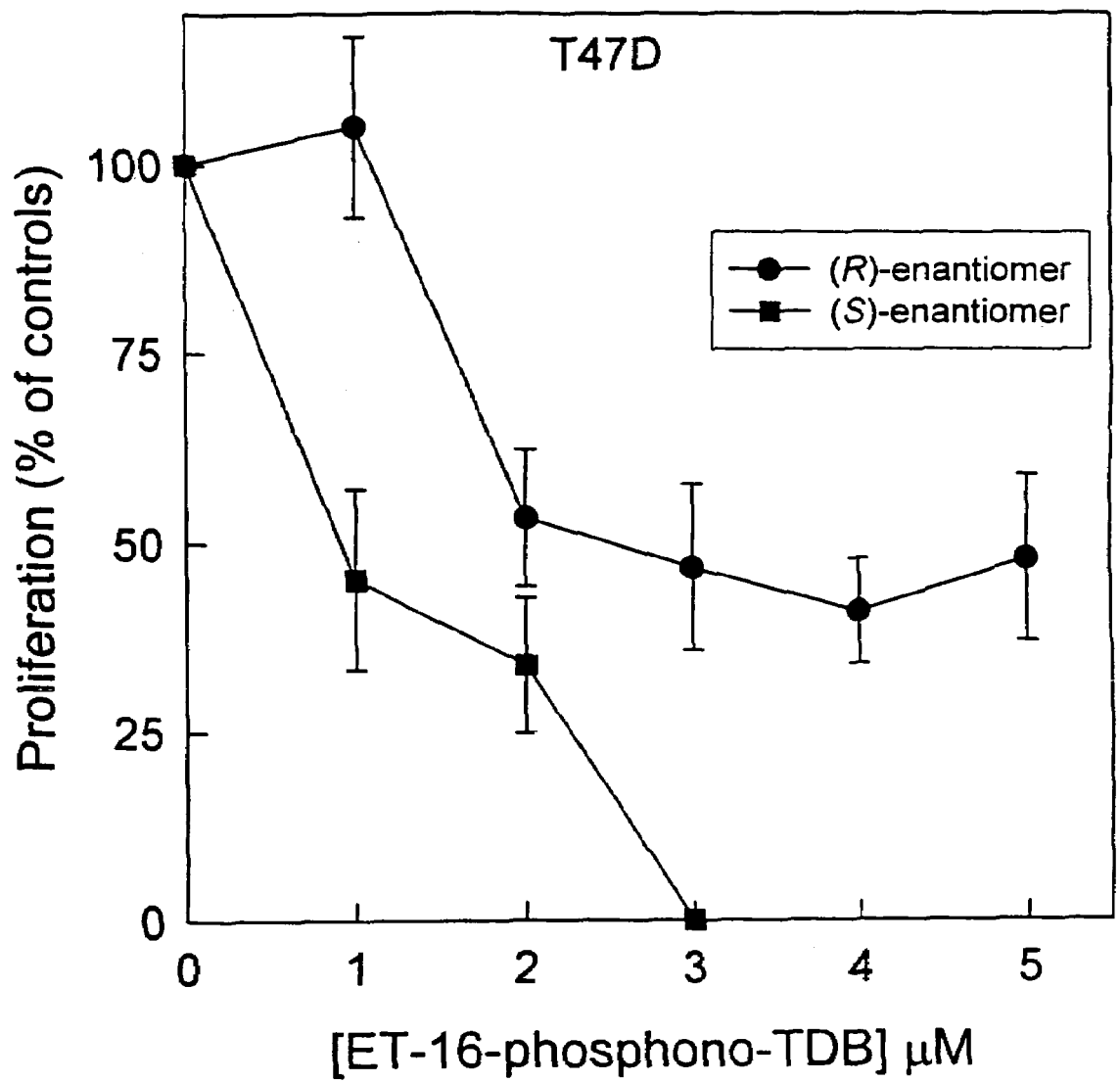
FIG. 3. Graphical depiction of the effects of (R) and (S) ET-16-phosphono-TDB on the proliferation of breast epithelial cancer cell line T47D.
Figure 4:
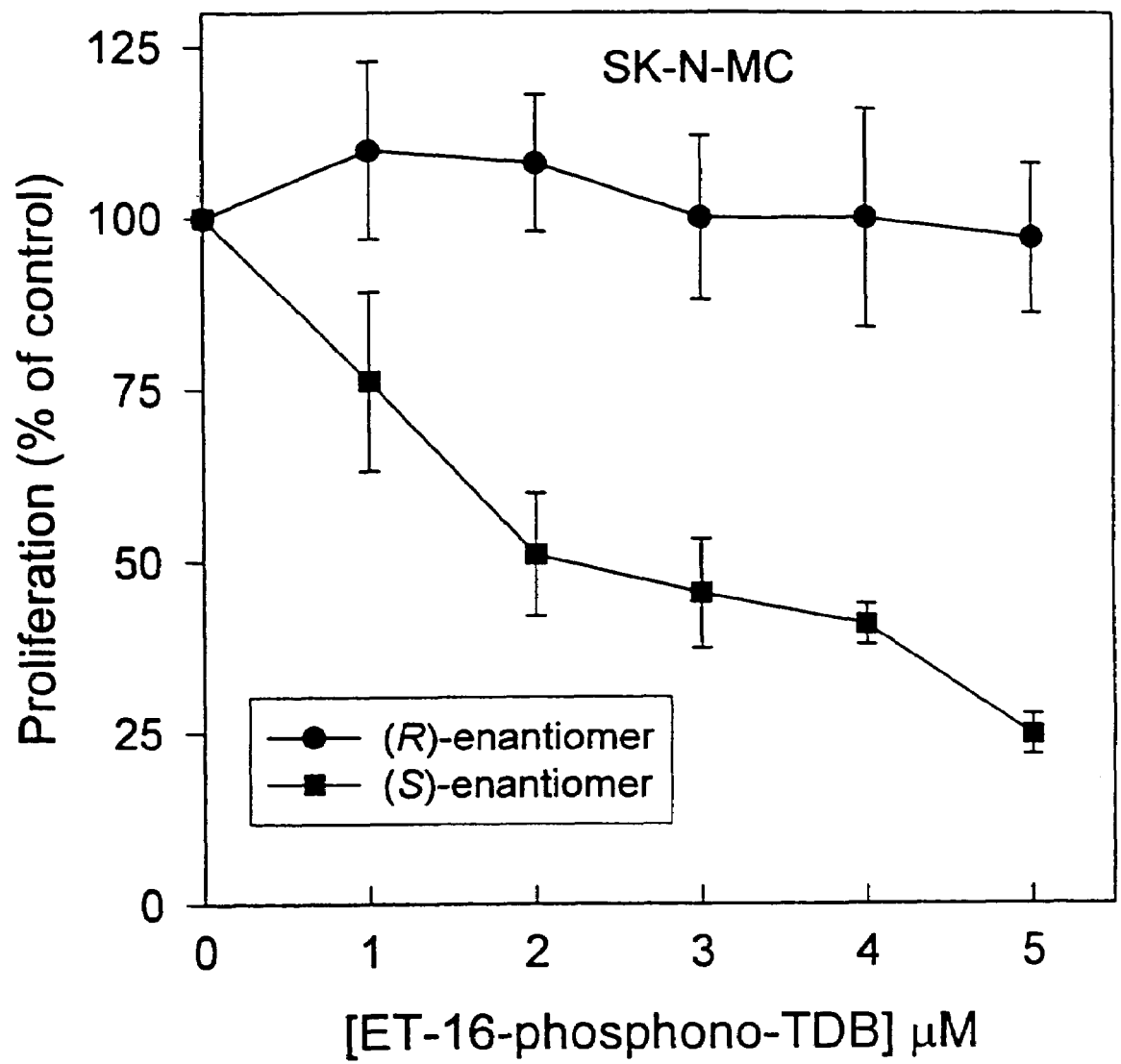
FIG. 4. Graphical depiction of the effects of (R) and (S) ET-16-phosphono TDB on the proliferation of neuroblastoma cell line SK-N-MC.
Figure 5:
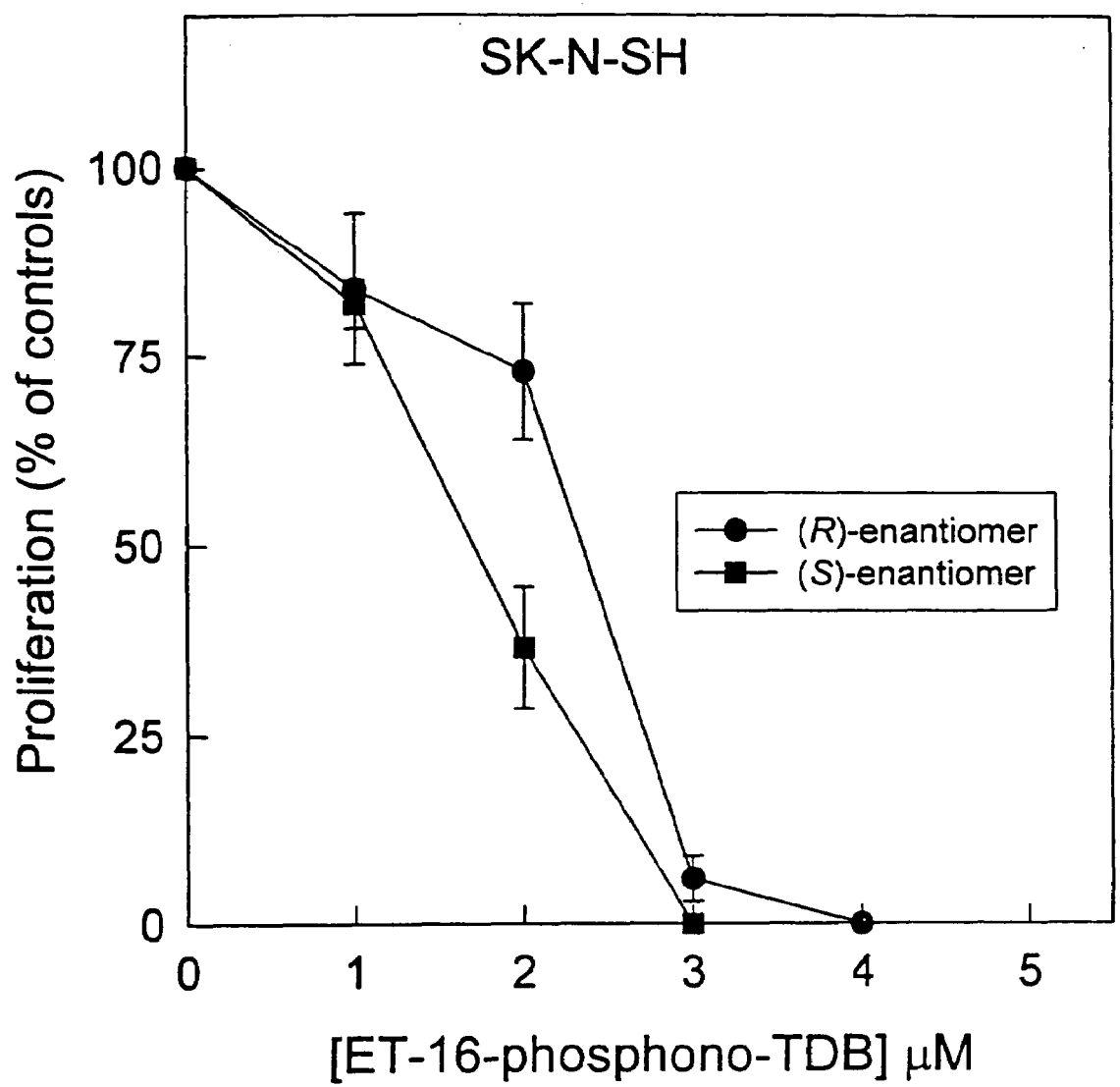
FIG. 5. Graphical depiction of the effects of (R) and (S) ET-16-phosphono-TDB on the proliferation of neuroblastoma cell line SK-N-SH.

Effect of (R)-ET-16-phosphono-TDB and (S)-ET-16-phosphono-TDB on Epithelial Cancer Cell Proliferation The antiproliferative properties of (R)- and (S)-ET-16-phosphono-TDB were assessed with breast epithelial cancer cells (FIGS. 1, 2, and 3) and neuroblastoma cell lines (FIGS. 4 and 5). The results are the means±standard deviations of quadruplicate wells from 3 different experiments.

Differences in the susceptibility of the cell lines to each enantiomer were observed at the concentrations examined. The order of increasing susceptibility among the breast cell lines was MDA-MB-468<MCF-7<T47D, and among neuroblastoma cell lines, it was SK-N-MC<SK-N-SH.

In the 3 breast epithelial cancer cell lines examined (MDA-MB-468, MCF-7 and T47D), the (S) enantiomer had a greater effect on inhibition of cell proliferation than did the R enantiomer (FIGS. 1-3) although the magnitude of the differences varied with the cell line. Thus, the S enantiomer was much more active than the R enantiomer in T47D and MDA-MB-468 cells compared with MCF-7 cells. The $IC_{50}$ values (drug concentration required to reduce cell growth by 50%) are shown in Table 1. A greater differential effect was also observed with the neuroblastoma cell line SK-N-MC than with SK-N-SH. Thus, for each cell line tested, the S enantiomer of ET-16-phosphono-TDB was significantly more active than the R enantiomer.

TABLE I

| Cell Line | $IC_{50}$ values (µM) | |
|---|---|---|
| | R-enantiomer | S-enantiomer |
| T47D | >5 | 0.9 |
| MDA-MB-468 | >5 | 4.2 |
| MCF-7 | 4.1 | 1.9 |
| SK-N-MC | >5 | 2.2 |
| SK-N-SH | 2.5 | 1.8 |

Example 4

Effect of S and R ET-16-phosphono-TDB Compounds on MAP kinase and PKB phosphorylation Quiescent MCF-7 cells were preincubated with ("+" in FIGS. 6-8) or without ("−" in FIGS. 6-8) 15 µM of the R or S enantiomer of ET-16-phosphono-TDB (TDB-PC in FIGS. 7-9) in DMEM supplemented with BSA (0.5 mg/mL) for 3 h. The cells were washed twice and stimulated with epithelial growth factor (EGF) or insulin for various periods. At the end of the incubation, the medium was aspirated, and the cells washed with ice-cold PBS and scraped into ice cold buffer comprising 20 mM Tris-HCl (pH 7.4) 2 mM EGTA, 100 mM β-glycerophosphate, 1 mM $Na_3VO_4$, aprotinin (10 µg/mL), leupeptin (10 µg/mL), 0.2 mM aininoethylbenzylsulfonyl fluoride, 0.2 mM benzarnidine, 1 mM dithiothreitol, 1% triton-X-100, and 0.5% NP-40). After ultrasonication, the mixture was centrifuged at 100,000×g for 30 min. The cell lysates were flash frozen and stored at −70° C. until required.

MAP kinase activity in cell lysates from EGF and insulin-stimulated MCF-7 cells were assessed by Western blot analysis with phospho-specific antibodies according to the instructions provided by the manufacturer (New England Biolabs). PKB/AKT activity in insulin-stimulated MCF-7 cell lysates was also assessed with phospho-specific antibodies by Western blot analysis. Bound antibody was visualized by chemiluminescence using reagents from Boehringer Mannheim and quantitated with a multiimager Fluor S system (BioRad).

Figure 6:
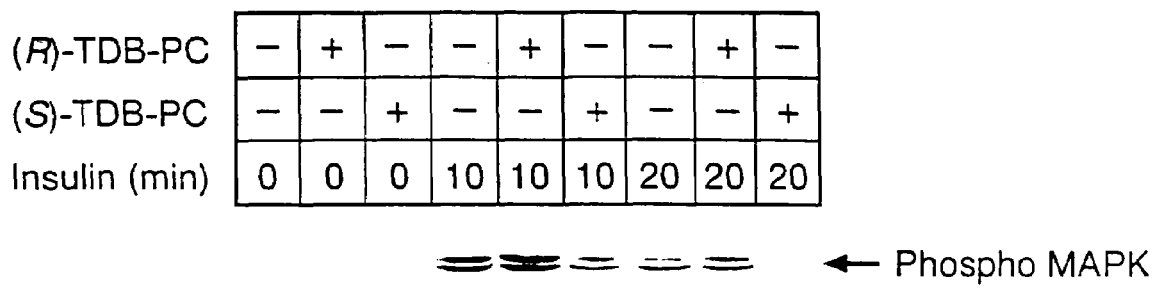
FIG. 6. Western blot analysis showing the effect of ET-16-phosphono-TDB preincubation on MAP kinase phosphorylation in insulin-stimulated MCF-7 cells. Cell lysates of quiescent MCF-7 cells, treated with ("+") or without ("−") (R)- or (S)-ET-16-phosphono-TDB and stimulated with insulin, were probed with anti-phospho-MAP kinase antibody.
Figure 7:
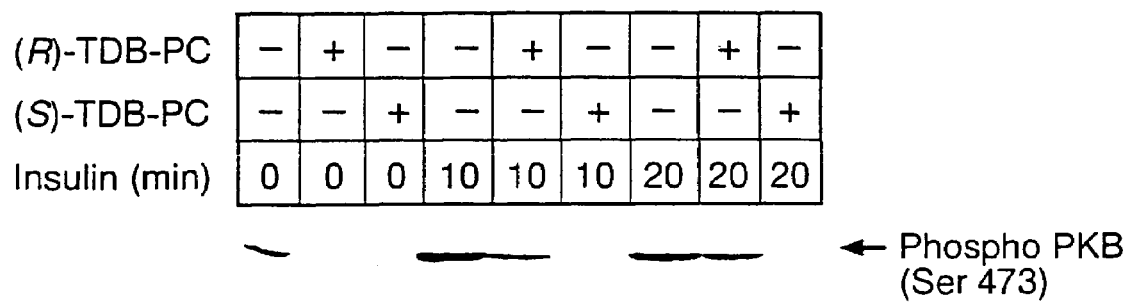
FIG. 7. Western, blot analysis showing the effect of ET-16-phosphono-TDB preincubation on PKB/AKT phosphorylation in insulin-stimulated MCF-7 cells. Cell lysates of quiescent MCF-7 cells, treated with ("+") or without ("−") (R)- or (S)-ET-16-phosphono-TDB and stimulated with insulin, were probed with anti-phospho-PKB/AKT antibody.
Figure 8:
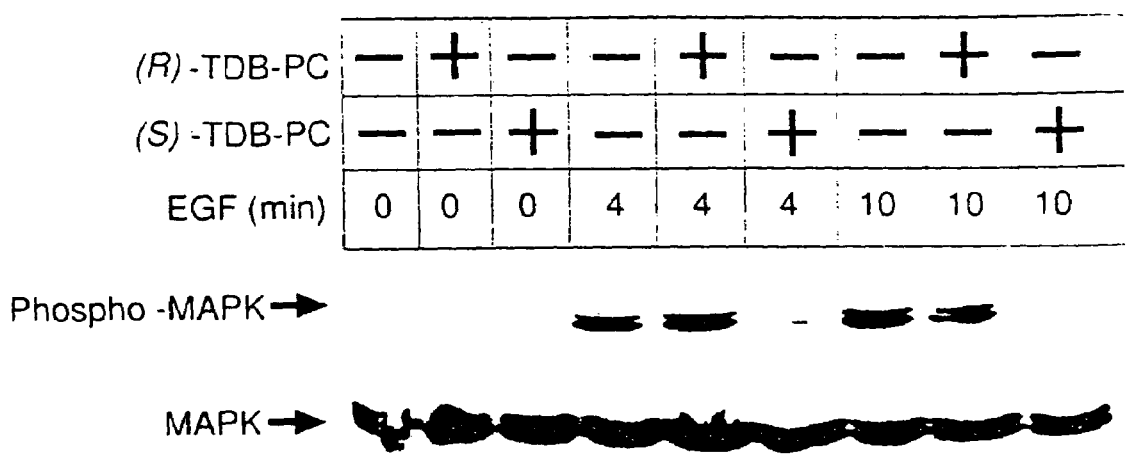
FIG. 8. Western blot analysis showing the effect of ET-16-phosphono-TDB preincubation on MAP kinase phosphorylation in EGF-stimulated MCF-7 cells. Cell lysates of quiescent MCF-7 cells, treated with ("+") or without ("−") (R)- or (S)-ET-16-phosphono-TDB and stimulated with EGF, were probed with anti-phospho-MAP kinase antibody and anti MAP kinase antibody.

The results displayed in FIGS. 6-8 indicate that there was a direct correlation between the activity of the compounds and inhibition of the MAP kinase pathway (which transduces signals from growth factors) and activation of protein kinase B pathway (which has been implicated in cell survival). The S enantiomer, which was more potent in inhibiting the growth of the cells, inhibited the phosphorylation of MAP kinase and PKB in insulin- and EGF-stimulated MCF-7 cells to a greater extent than the less active R enantiomer. The results suggest that the inhibitory effects of the compounds are related to their ability to inhibit MAP kinase, which is implicated in proliferation (Marshall (1995) *Cell* 80: 179-185), and the PKB pathway, which is implicated in cell survival (Coffer et al. (1998) *Biochem. J.* 335: 1-13).

Example 5

Growth Inhibition ($GI_{50s}$)

For growth inhibitory evaluation, five human tumor cell lines (U937; HT29; A549; MCF7; MCF7/ADR) and two normal fibroblast cell lines (NIH-3T3, murine; WI-38, human) were used. For comparison, the activity of free L-ET18OCH$_3$ and D-ET18OCH$_3$ was examined. As shown in Table 3, both L and D isomers of ET18OCH$_3$ gave essentially identical results with the order of sensitivity for the cells lines being U937>HT29>A549>MCF7>MCF7/ADR, NIH-3T3 (normal cell line). WI-38 cells were moderately sensitive to both ether lipids with GI50 values of 10-13 µM, which was 3-4 times lower than that for the NIH-3T3 cells at 41-47 µM.

Compounds (R)- and (S)-ET-16-phosphono-TDB show remarkable selectivity with significantly higher $GI_{50}$ values for the normal cell lines as compared to the tumor cell lines.

TABLE 2

Growth Inhibition of Tumor/Normal Cells

| | GI50 (µM) | | | | | | |
|---|---|---|---|---|---|---|---|
| | Tumor Cell Lines | | | | | Normal Cell Lines* | |
| Compound | U937 | HT29 | A549 | MCF7 | MCF7/ADR | NIH-3T3 | WI38 |
| L-ET18OCH$_3$ | 1.0-1.5 | 5.5, 6.0 | 6.5-9.1 | 9.7-18.6 | 25.7->40 | 46.6 | 10-12.8 |
| D-ET18OCH$_3$ | 1.4 | 5.1 | 8.0 | 14.6 | 25.1 | 41.4 | 10-13.5 |
| (R)-ET-16-phosphono-TDB | 2.2 | 5.9 | 15.3 | 35.1 | >40 | 77.3 | 57.5 |
| (S)-ET-16-phosphono-TDB | 1.1 | 2.8 | 9.0 | 32.4 | >40 | 66.3 | 14.4 |

The invention has been described with reference to specific embodiments. Substitutions, omissions, additions and deletions may be made without departing from the spirit and scope of the invention defined in the appended claims. From the foregoing description, various modifications and changes in the composition and method will occur to those skilled in the art. All such modifications coming within the scope of the appended claims are intended to be included therein.

All of the above publications, patents and patent applications are herein incorporated by reference in their entirety to the same extent as if each individual publication, patent or patent application was specifically and individually indicated to be incorporated by reference in its entirety.

The invention claimed is:

1. A compound of the formula I, or a pharmaceutically acceptable salt, prodrug or isomer thereof:

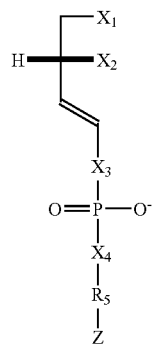

I wherein
$X_1$ is H, $R_1$, $R_2$, $OR_2$, $NR_1R_2$, or $S(O)_aR_2$, where a is an integer selected from 0, 1, 2, or 3;
$X_2$ is H, $R_3$, $R_4$, $OR_4$, $NR_3R_4$, or $S(O)_aR_4$, where a is an integer selected from 0, 1, 2, or 3;
$X_3$ is $(CH_2)_b$, where b is an integer selected from 0, 1, 2, 3, or 4;
$X_4$ is $(CH_2)_c$, where c is an integer selected from 0, 1, 2, 3, or 4;
$R_1$ is a straight-chain or branched alkyl having 12 to 20 carbon atoms or a straight-chain or branched alkenyl group having 12 to 20 carbon atoms;
$R_2$ is H, a straight-chain or branched alkyl having 12 to 20 carbon atoms or a straight-chain or branched alkenyl group having 12 to 20 carbon atoms;
$R_3$ is a straight-chain alkyl group having 1 to 3 carbon atoms, or a branched or cyclic alkyl group having 3 carbon atoms;
$R_4$ is H, a straight-chain alkyl group having 1 to 3 carbon atoms, or a branched or cyclic alkyl group having 3 carbon atoms;
$R_5$ is $(CH_2)_m$ where m is an integer selected from 0, 1, 2, 3, or 4;
Z is H,

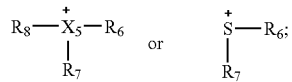

$X_5$ is N or As;
$R_6$ and $R_7$ are each independently hydrogen, a straight-chain alkyl group having 1 to 3 carbon atoms, or a branched or cyclic alkyl group having 3 carbon atoms; and
$R_8$ is hydrogen, a straight-chain alkyl group having 1 to 3 carbon atoms or a branched or cyclic alkyl group having 3 carbon atoms.

2. The compound of claim 1 further comprising a pharmaceutically acceptable anion.

3. The compound of claim 1, wherein $R_1$ and $R_2$ are each independently a straight-chain or branched alkyl having 16 to 20 carbon atoms, or a straight-chain or a branched alkenyl group having 16 to 20 carbon atoms.

4. The compound of claim 3, wherein $R_1$ and $R_2$ are each independently a straight-chain or branched alkyl having 18 carbon atoms, or a straight-chain or a branched alkenyl group having 18 carbon atoms.

5. A compound of the formula I, or a pharmaceutically acceptable salt, prodrug or isomer thereof:

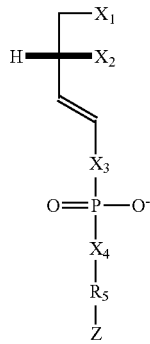

I wherein
$X_1$ is $OR_2$ or $NHR_2$;
$X_2$ is H, $R_3$, $R_4$, $OR_4$, $NR_3R_4$, or $S(O)_aR_4$, where a is an integer selected from 0, 1, 2, or 3;
$X_3$ is $(CH_2)_b$, where b is an integer selected from 0, 1, 2, 3, or 4;
$X_4$ is $(CH_2)_c$ where c is an integer selected from 0, 1, 2, 3, or 4;
$R_1$ is a straight-chain or branched alkyl having 12 to 20 carbon atoms or a straight-chain or branched alkenyl group having 12 to 20 carbon atoms;
$R_2$ is a straight-chain or branched alkyl having 16 to 20 carbon atoms, or a straight-chain or a branched alkenyl group having 16 to 20 carbon atoms;
$R_3$ is a straight-chain alkyl group having 1 to 3 carbon atoms, or a branched or cyclic alkyl group having 3 carbon atoms;
$R_4$ is H, a straight-chain alkyl group having 1 to 3 carbon atoms, or a branched or cyclic alkyl group having 3 carbon atoms;
$R_5$ is $(CH_2)_m$ where m is an integer selected from 0, 1, 2, 3, or 4;

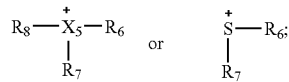

$X_5$ is N or As;

$R_6$ and $R_7$ are each independently hydrogen, a straight-chain alkyl group having 1 to 3 carbon atoms, or a branched or cyclic alkyl group having 3 carbon atoms; and $R_8$ is hydrogen, a straight-chain alkyl group having 1 to 3 carbon atoms or a branched or cyclic alkyl group having 3 carbon atoms.

6. The compound of claim 5, wherein $X_1$ is $OR_2$ or $NHR_2$, and wherein $R_2$ is a straight-chain or branched alkyl having 18 carbon atoms, or a straight-chain or a branched alkenyl group having 18 carbon atoms.

7. A compound of the formula I, or a pharmaceutically acceptable salt, prodrug or isomer thereof:

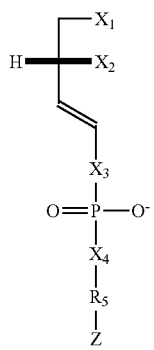

I wherein $X_1$ or $X_2$ is $-SR_2$, $-S(=O)R_2$, $-S(=O)_2R_2$, $-S(=O)_2OR_2$, $-OS(=O)_2R_2$ or $-OCH_3$;

$X_3$ is $(CH_2)_b$, where b is an integer selected from 0, 1, 2, 3, or 4;

$X_4$ is $(CH_2)_c$, where c is an integer selected from 0, 1, 2, 3, or 4;

$R_1$ is a straight-chain or branched alkyl having 12 to 20 carbon atoms or a straight-chain or branched alkenyl group having 12 to 20 carbon atoms;

$R_2$ is H, a straight-chain or branched alkyl having 12 to 20 carbon atoms or a straight-chain or branched alkenyl group having 12 to 20 carbon atoms;

$R_3$ is a straight-chain alkyl group having 1 to 3 carbon atoms, or a branched or cyclic alkyl group having 3 carbon atoms;

$R_4$ is H, a straight-chain alkyl group having 1 to 3 carbon atoms, or a branched or cyclic alkyl group having 3 carbon atoms;

$R_5$ is $(CH_2)_m$ where m is an integer selected from 0, 1, 2, 3 or 4;

Z is H,

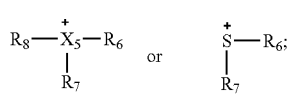

$X_5$ is N or As;

$R_6$ and $R_7$ are each independently hydrogen, a straight-chain alkyl group having 1 to 3 carbon atoms, or a branched or cyclic alkyl group having 3 carbon atoms; and $R_8$ is hydrogen, a straight-chain alkyl group having 1 to 3 carbon atoms or a branched or cyclic alkyl group having 3 carbon atoms.

8. The compound of claim 1, wherein $X_3$, $X_4$, and $R_5$ are each independently a direct link, a $-CH_2-$ group, or a $-CH_2CH_2-$ group.

9. The compound of claim 1, wherein Z is

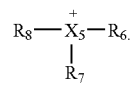

10. The compound of claim 1, wherein Z is

11. A compound of the formula I, or a pharmaceutically acceptable salt, prodrug or isomer thereof:

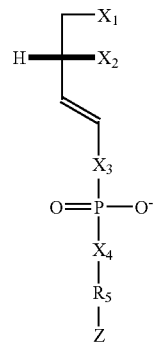

I wherein $X_1$ is O;

$X_2$ is O;

$X_3$ is $(CH_2)_b$ and b is 0;

$X_4$ is O;

$R_1$ is a straight-chain or branched alkyl having 12 to 20 carbon atoms or a straight-chain or branched alkenyl group having 12 to 20 carbon atoms;

$R_2$ is H, a straight-chain or branched alkyl having 12 to 20 carbon atoms or a straight-chain or branched alkenyl group having 12 to 20 carbon atoms;

$R_3$ is a straight-chain alkyl group having 1 to 3 carbon atoms, or a branched or cyclic alkyl group having 3 carbon atoms;

$R_4$ is H, a straight-chain alkyl group having 1 to 3 carbon atoms, or a branched or cyclic alkyl group having 3 carbon atoms;

$R_5$ is $(CH_2)_m$ where m is an integer selected from 0, 1, 2, 3 or 4;

Z is H,

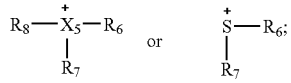

$X_5$ is N or As;

$R_6$ and $R_7$ are each independently hydrogen, a straight-chain alkyl group having 1 to 3 carbon atoms, or a branched or cyclic alkyl group having 3 carbon atoms; and $R_8$ is hydrogen, a straight-chain alkyl group having 1 to 3 carbon atoms or a branched or cyclic alkyl group having 3 carbon atoms.

12. The compound of claim 1, wherein the compound is optically active, and substantially free of the R enantiomer.

13. The compound of claim 1, wherein the compound is optically active and substantially free of the S enantiomer.

14. The compound 2'-(trimethylammonio)ethyl 4-(hexadecyloxy)-3-(S)-methoxy-1-butenephosphonate substantially free of the R enantiomer.

15. The compound 2'-(trimethylammonio)ethyl 4-(hexadecyloxy)-3-(S)-methoxy-1-butenephosphonate substantially free of the S enantiomer.

16. A pharmaceutical composition comprising a pharmaceutically acceptable carrier and a pharmaceutically effective amount of a compound of claim 1.

17. A method of inhibiting proliferation of tumor cells in a mammal afflicted with a cancer which comprises administering to the mammal a therapeutically effective amount of the pharmaceutical composition of claim 16, comprising from about 0.1 to about 1000 mg of the compound of claim 1 per kg of the body weight of the mammal per day.

18. A method of claim 17, wherein the cancer is selected from the group consisting of lung cancers, brain cancers, colon cancers, ovarian cancers, breast cancers, leukemias, lymphomas, sarcomas, and carcinomas.

19. The method of claim 17, comprising administering to the mammal an additional biologically active agent.

20. The method of claim 19, wherein the additional biologically active agent is selected from the group consisting of antineoplastic agents, antimicrobial agents, and hematopoietic cell growth stimulating agents.

21. A compound of formula II, or a pharmaceutically acceptable salt, prodrug or isomer thereof:

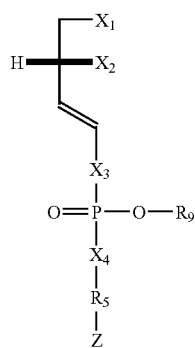

wherein $X_1$ is H, $R_1$, $R_2$, $OR_2$, $NR_1R_2$, or $S(O)_aR_2$, where a is an integer selected from 0, 1, 2, or 3;

$X_2$ is H, $R_3$, $R_4$, $OR_4$, $NR_3R_4$, or $S(O)_aR_4$, where a is an integer selected from 0, 1, 2, or 3;

$X_3$ is $(CH_2)_b$, where b is an integer selected from 0, 1, 2, 3, or 4;

$X_4$ is $(CH_2)_c$, where c is an integer selected from 0, 1, 2, 3, or 4;

$R_1$ is a straight-chain or branched alkyl having 12 to 20 carbon atoms or a straight-chain or branched alkenyl group having 12 to 20 carbon atoms;

$R_2$ is H, a straight-chain or branched alkyl having 12 to 20 carbon atoms or a straight-chain or branched alkenyl group having 12 to 20 carbon atoms;

$R_3$ is a straight-chain alkyl group having 1 to 3 carbon atoms, or a branched or cyclic alkyl group having 3 carbon atoms;

$R_4$ is H, a straight-chain alkyl group having 1 to 3 carbon atoms, or a branched or cyclic alkyl group having 3 carbon atoms;

$R_5$ is $(CH_2)_m$ where m is an integer selected from 0, 1, 2, 3, or 4;

Z is H,

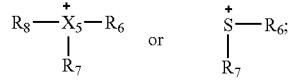

$X_5$ is N or As;

$R_6$ and $R_7$ are each independently hydrogen, a straight-chain alkyl group having 1 to 3 carbon atoms, or a branched or cyclic alkyl group having 3 carbon atoms;

$R_8$ is hydrogen, a straight-chain alkyl group having 1 to 3 carbon atoms or a branched or cyclic alkyl group having 3 carbon atoms; and $R_9$ is a straight-chain alkyl group having 1 to 3 carbon atoms or a branched or cyclic alkyl group having 3 carbon atoms.

22. The compound of claim 21 further comprising a pharmaceutically acceptable anion.

23. The compound of claim 21, wherein $R_1$ and $R_2$ are each independently a straight-chain or branched alkyl having 16 to 20 carbon atoms, or a straight-chain or a branched alkenyl group having 16 to 20 carbon atoms.

24. The compound of claim 23, wherein $R_1$ and $R_2$ are each independently a straight-chain or branched alkyl having 18 carbon atoms, or a straight-chain or a branched alkenyl group having 18 carbon atoms.

25. A compound of the formula II, or a pharmaceutically acceptable salt, prodrug or isomer thereof:

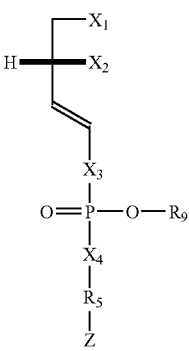

wherein
- $X_1$ is $OR_2$ or $NHR_2$;
- $X_2$ is H, $R_3$, $R_4$, $OR_4$, $NR_3R_4$, or $S(O)_aR_4$, where a is an integer selected from 0, 1, 2, or 3;
- $X_3$ is $(CH_2)_b$, where b is an integer selected from 0, 1, 2, 3, or 4;
- $X_4$ is $(CH_2)_c$, where c is an integer selected from 0, 1, 2, 3, or 4;
- $R_1$ is a straight-chain or branched alkyl having 12 to 20 carbon atoms or a straight-chain or branched alkenyl group having 12 to 20 carbon atoms;
- $R_2$ is H, a straight-chain or branched alkyl having 12 to 20 carbon atoms or a straight-chain or branched alkenyl group having 12 to 20 carbon atoms;
- $R_3$ is a straight-chain alkyl group having 1 to 3 carbon atoms, or a branched or cyclic alkyl group having 3 carbon atoms;
- $R_4$ is H, a straight-chain alkyl group having 1 to 3 carbon atoms, or a branched or cyclic alkyl group having 3 carbon atoms;
- $R_5$ is $(CH_2)_m$ where m is an integer selected from 0, 1, 2, 3, or 4;
- Z is H,

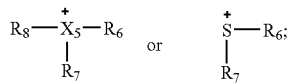

- $X_5$ is N or As;
- $R_6$ and $R_7$ are each independently hydrogen, a straight-chain alkyl group having 1 to 3 carbon atoms, or a branched or cyclic alkyl group having 3 carbon atoms;
- $R_8$ is hydrogen, a straight-chain alkyl group having 1 to 3 carbon atoms or a branched or cyclic alkyl group having 3 carbon atoms; and
- $R_9$ is a straight-chain alkyl group having 1 to 3 carbon atoms or a branched or cyclic alkyl group having 3 carbon atoms.

26. The compound of claim 25, wherein $X_1$ is $OR_2$ or $NHR_2$, and wherein $R_2$ is a straight-chain or branched alkyl having 18 carbon atoms, or a straight-chain or a branched alkenyl group having 18 carbon atoms.

27. A compound of the formula II, or a pharmaceutically acceptable salt, prodrug or isomer thereof:

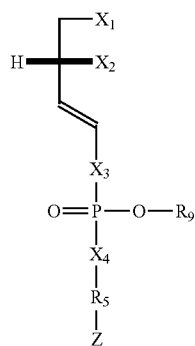

wherein
- $X_1$ or $X_2$ is $-SR_2$, $-S(=O)R_2$, $-S(=O)_2R_2$, $-S(=O)_2OR_2$, $-OS(=O)_2R_2$ or $-OCH_3$;
- $X_3$ is $(CH_2)_b$, where b is an integer selected from 0, 1, 2, 3, or 4;
- $X_4$ is $(CH_2)_c$, where c is an integer selected from 0, 1, 2, 3, or 4;
- $R_1$ is a straight-chain or branched alkyl having 12 to 20 carbon atoms or a straight-chain or branched alkenyl group having 12 to 20 carbon atoms;
- $R_2$ is H, a straight-chain or branched alkyl having 12 to 20 carbon atoms or a straight-chain or branched alkenyl group having 12 to 20 carbon atoms;
- $R_3$ is a straight-chain alkyl group having 1 to 3 carbon atoms, or a branched or cyclic alkyl group having 3 carbon atoms;
- $R_4$ is H, a straight-chain alkyl group having 1 to 3 carbon atoms, or a branched or cyclic alkyl group having 3 carbon atoms;
- $R_5$ is $(CH_2)_m$ where m is an integer selected from 0, 1, 2, 3, or 4;
- Z is H,

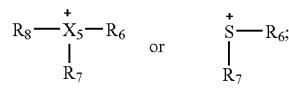

- $X_5$ is N or As;
- $R_6$ and $R_7$ are each independently hydrogen, a straight-chain alkyl group having 1 to 3 carbon atoms, or a branched or cyclic alkyl group having 3 carbon atoms;
- $R_8$ is hydrogen, a straight-chain alkyl group having 1 to 3 carbon atoms or a branched or cyclic alkyl group having 3 carbon atoms; and
- $R_9$ is a straight-chain alkyl group having 1 to 3 carbon atoms or a branched or cyclic alkyl group having 3 carbon atoms.

28. The compound of claim 21, wherein $X_3$, $X_4$, and $R_5$ are each independently a direct link, a $-CH_2-$ group, or a $-CH_2CH_2-$ group.

29. The compound of claim 21, wherein Z is

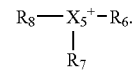

30. The compound of claim 26, wherein Z is $R_7-S^+-R_6$.

31. A compound of the formula II, or a pharmaceutically acceptable salt, prodrug or isomer thereof:

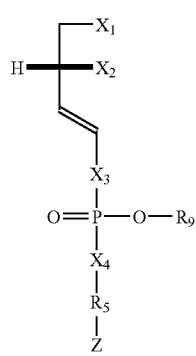

wherein
X$_1$ is O;
X$_2$ is O;
X$_3$ is (CH$_2$)$_b$ and is 0;
X$_4$ is O;
R$_1$ is a straight-chain or branched alkyl having 12 to 20 carbon atoms or a straight-chain or branched alkenyl group having 12 to 20 carbon atoms;
R$_2$ is H, a straight-chain or branched alkyl having 12 to 20 carbon atoms or a straight-chain or branched alkenyl group having 12 to 20 carbon atoms;
R$_3$ is a straight-chain alkyl group having 1 to 3 carbon atoms, or a branched or cyclic alkyl group having 3 carbon atoms;
R$_4$ is H, a straight-chain alkyl group having 1 to 3 carbon atoms, or a branched or cyclic alkyl group having 3 carbon atoms;
R$_5$ is (CH$_2$)$_m$ where m is an integer selected from 0, 1, 2, 3, or 4;
Z is H,

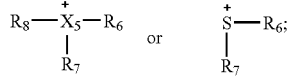

X$_5$ is N or As;
R$_6$ and R$_7$ are each independently hydrogen, a straight-chain alkyl group having 1 to 3 carbon atoms, or a branched or cyclic alkyl group having 3 carbon atoms;
R$_8$ is hydrogen, a straight-chain alkyl group having 1 to 3 carbon atoms or a branched or cyclic alkyl group having 3 carbon atoms; and
R$_9$ is a straight-chain alkyl group having 1 to 3 carbon atoms or a branched or cyclic alkyl group having 3 carbon atoms.

32. The compound of claim 21, wherein the compound is optically active, and substantially free of the R enantiomer.

33. The compound of claim 21, wherein the compound is optically active and substantially free of the S enantiomer.

34. A pharmaceutical composition comprising a pharmaceutically acceptable carrier and a pharmaceutically effective amount of a compound of claim 33.

35. A method of inhibiting proliferation of tumors cells in a mammal afflicted with a cancer which comprises administering to the mammal a therapeutically effective amount of the pharmaceutical composition of claim 34, comprising from about 0.1 to about 1000 mg of the compound of claim 1 per kg of the body weight of the mammal per day.

36. A method of claim 35, wherein the cancer is selected from the group consisting of lung cancers, brain cancers, colon cancers, ovarian cancers, breast cancers, leukemias, lymphomas, sarcomas, and carcinomas.

37. The method of claim 36, comprising administering to the mammal an additional biologically active agent.

38. The method of claim 37, wherein the additional biologically active agent is selected from the group consisting of antineoplastic agents, antimicrobial agents, and hematopoietic cell growth stimulating agents.

39. A method for making 2'-(trimethylammonio)ethyl 4-(hexadecyloxy)-3-(S)-methoxy-1-butenephosphonate substantially free of the (R) enantiomer, comprising:
   (i) oxidizing 1-O-hexadecyl-2-O-methyl-sn-glycerol under Swern oxidation conditions sufficient to produce (S)-1-O-hexadecyl-2-O-methoxyglyceraldehyde;
   (ii) reacting the (S)-1-O-hexadecyl-2-O-methoxyglyceraldehyde with tetraisopropyl methylenediphosphonate under conditions sufficient to produce diisopropyl 4-(hexadecyloxy)-3-(S)-methoxy-1-butenephosphonate;
   (iii) hydrolyzing the diisopropyl 4-(hexadecyloxy)-3-(S)-methoxy-1-butenephosphonate under conditions sufficient to produce the 4-(hexadecyloxy)-3-(S)-methoxy-1-butenephosphonic acid; and
   (iv) reacting the diisopropyl 4-(hexadecyloxy)-3-(S)-methoxy-1-butenephosphonate with choline tosylate under conditions sufficient to produce 2'-(trimethylammonio)ethyl 4-(hexadecyloxy)-3-(S)-methoxy-1-butenephosphonate.

40. A method for making 2'-(trimethylammonio)ethyl 4-(hexadecyloxy)-3-(S)-methoxy-1-butenephosphonate substantially free of the (S) enantiomer, comprising:
   (i) oxidizing 3-O-hexadecyl-2-O-methyl-sn-glycerol under Swern oxidation conditions sufficient to produce (S)-1-O-hexadecyl-2-O-methoxyglyceraldehyde;
   (ii) reacting the (S)-1-O-hexadecyl-2-O-methoxyglyceraldehyde with tetraisopropyl methylenediphosphonate under conditions sufficient to produce diisopropyl 4-(hexadecyloxy)-3-(S)-methoxy-1-butenephosphonate;
   (iii) hydrolyzing the diisopropyl 4-(hexadecyloxy)-3-(S)-methoxy-1-butenephosphonate under conditions sufficient to produce the 4-(hexadecyloxy)-3-(S)-methoxy-1-butenephosphonic acid; and
   (iv) reacting the diisopropyl 4-(hexadecyloxy)-3-(S)-methoxy-1-butenephosphonate with choline tosylate under conditions sufficient to produce 2'-(trimethylammonio)ethyl 4-(hexadecyloxy)-3-(S)-methoxy-1-butenephosphonate.

41. The method according to claim 17 wherein said cancer is breast epithelial cancer.

42. The method according to claim 17 wherein said cancer is a neuroblastoma.

43. The method according to claim 35 wherein said cancer is breast epithelial cancer.

44. The method according to claim 35 wherein said cancer is a neuroblastoma.

* * * * *